United States Patent [19]

Dorn et al.

[11] Patent Number: 4,728,607

[45] Date of Patent: Mar. 1, 1988

[54] MINIATURIZED YEAST IDENTIFICATION SYSTEM

[75] Inventors: Gordon L. Dorn; William H. Fleming; Karen L. Knezek, all of Dallas, Tex.

[73] Assignee: J. K. and Susie L. Wadley Research Institute and Blood Bank, Dallas, Tex.

[21] Appl. No.: 592,072

[22] Filed: Mar. 22, 1984

[51] Int. Cl.⁴ .................... C12Q 1/04; C12M 1/22
[52] U.S. Cl. ........................ 435/34; 435/297; 435/298; 435/299; 435/300; 435/301; 350/536
[58] Field of Search ............... 435/297, 298, 299, 300, 435/301, 34; 350/536

[56] References Cited

U.S. PATENT DOCUMENTS

| | | | |
|---|---|---|---|
| 2,561,339 | 1/1944 | Chediak | 435/308 |
| 3,073,750 | 5/1959 | Greenblatt | 435/298 |
| 3,097,070 | 7/1963 | Aldrich et al. | 435/297 |
| 3,728,228 | 10/1971 | Duranty | 435/301 |
| 3,883,398 | 5/1975 | Ono | 435/301 |
| 3,883,425 | 5/1975 | Dorn | 210/23 |
| 3,928,136 | 12/1975 | Launey | 435/299 |
| 4,030,980 | 6/1977 | Beckford et al. | 435/301 |
| 4,144,133 | 3/1979 | Dorn et al. | 195/100 |
| 4,179,266 | 12/1979 | Lukacsek | 435/254 |

OTHER PUBLICATIONS

*Journal of Clinical Microbiology* 15:339 (Feb. 1982) Kaufmann and Merz.
*Mycopathologia* 76:83 (1981) Hrmova and Drobica.
*The American Journal of Medicine* 71:363 Meunier-Carpentier et al.
*Mycopathologia* 76:125 (1981) Casal and Linares
*Id.* 70:95 (1980) Hedden and Buck.
*American Journal of Clinical Pathologists* 73:578 (Apr. 1980) Kiehn et al.
*Journal of Clinical Microbiology* 10:380 (Sep. 1979) Zimmer and Roberts.
*Id.* 10:357 (Sep. 1979) Land et al.
*Id.* 9:565 (May 1979) Buesching et al.
*Id.* 7:584 (Jun. 1978) Roberts et al.
*Mycopathologia* 64:143 (1978) Gunasekaran and Hughes
*Id.* 61:151 (1977) Gunasekaran and Hughes.
*Journal of Clinical Microbiology* 5:501 (Apr. 1977) Warwood and Blazevic.
*Id.* 5:236 (Feb. 1977) Fleming III et al.
*Mycopathologia* 61:183 (1977) Auger and Joly.
*American Journal of Clinical Pathology* 67:269 (Mar. 1977) Zwadyk et al.
*Journal of Clinical Microbiology* (Jul. 1976) Bowman and Ahearn.
*Id.* 3:302 (Mar. 1976) Roberts et al.
*Medical Laboratory Technology* 32:23 (1975) Odds and Evans 20.
*Sabouraudia* 13:148 (1975) Lee et al.
*Journal of Clinical Microbiology* 2:345 (Oct. 1975) Beheshti et al.
*Id.* 2:354 (Oct. 1975) Bowman and Ahearn.
*Id.* 2:206 (Sep. 1975) Land et al.
*Id.* 2:96 (Aug. 1975) Hopfer and Groschel.
*Id.* 2.115 (Aug. 1975) Hofpfer and Blank.
*Infection and Immunity* 12:119 (Jul. 1975) Land et al.
*Journal of Clinical Microbiology* 1:509 (Jun. 1975) Chaskes and Tyndall.
*Infection and Immunity* 11:1014 (May 1975) Land et al.
*Canadian Journal of Microbiology* 21:338 (1975) Evans et al.
*Sabouraudia* 12:295 (1974) Nishioka and Silva-Hunter.
*American Journal of Medical Technology* 40:377 (Sep. 1974) Adams, Jr. and Cooper.
*Sabouraudia* 11:259 (1973) Joshi et al.
(List continued on next page.)

*Primary Examiner*—Sam Rosen
*Assistant Examiner*—William J. Herald
*Attorney, Agent, or Firm*—Richards, Harris, Medlock & Andrews

[57] ABSTRACT

A culture container having a convenient size for use under a conventional microscope stage. The container having media of a composition and amount effective to induce germ tube production in Cryptococcus. The media, which includes purified saponin, oxgall, a substrate for phenol oxidase, water and ammonia ions, is in an amount up to 5 milliliters at a depth up to 4.5 milliliters.

38 Claims, 13 Drawing Figures

OTHER PUBLICATIONS

*American Journal of Clinical Pathology* 60:839 (1973) Joshi et al.

*Surgery* 72:730 (Nov. 1972) Gaines et al.

*Archives of Surgery* 104:509 (Apr. 1972) MacMillian et al.

*Journal of General Microbiology* 67:255 (1971) Chattaway and Odds.

*American Journal of Clinical Pathology* 55:580 (May 1971) Dolan.

*Applied Microbiology* 21:541 (Mar. 1971) Korth and Pulverer.

*American Journal of Clinical Pathology* 55:733 (1971) Dolan et al.

*Journal of Bacteriology* 104:910 (Nov. 1970) Jansons and Nickerson.

*Id.* 100:701 (Nov. 1969) Mardon et al.

*Sabouraudia* 7:146 (Jun. 1969) Bernander and Edebo.

*Journal of General Microbiology* 51:367 (1968) Chattaway et al.

*Journal of Investigative Dermatology* 44:171 (1965) Landau et al.

*Sabouraudia* 4:126 (Jun. 1965) Mackenzie.

*Mycopathologia* 23:197 (1964) Widra.

*Sabouraudia* 2:205 (1963) Buckley and Uden.

*American Journal of Medical Technology* 4:199 (Jul.-Aug. 1963) Ducan and Floeder.

*Zeitschrift f. Hygiene* 148:466 (1962) Staib (German article).

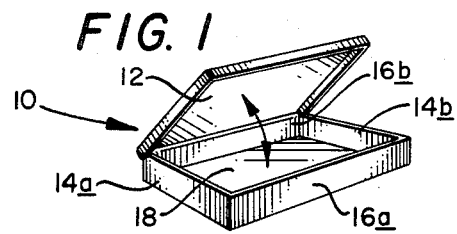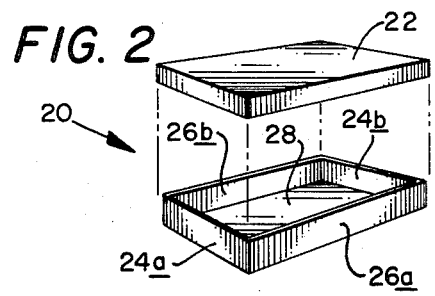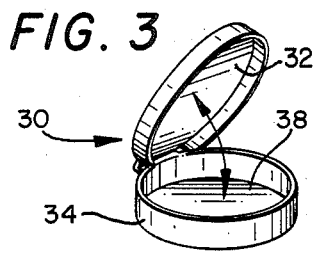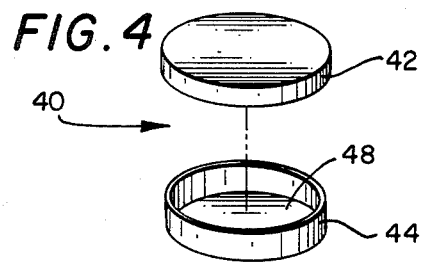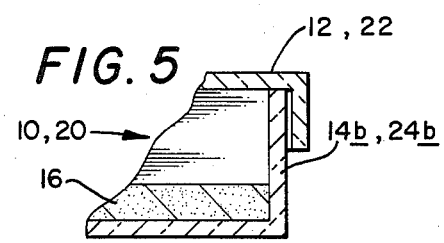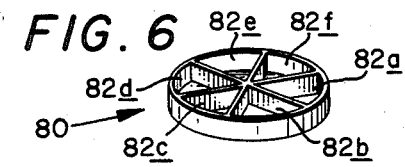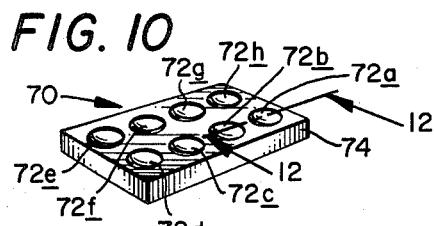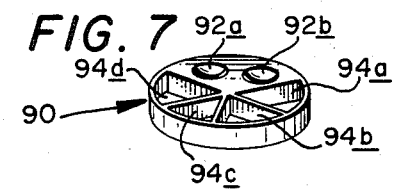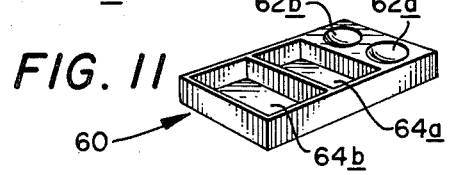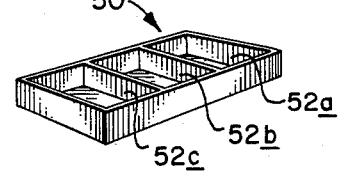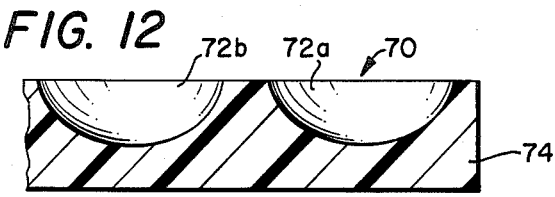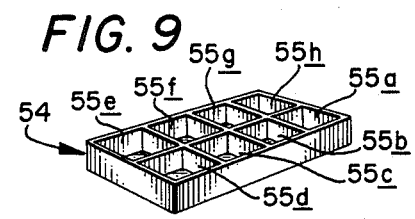

MINIATURIZED YEAST IDENTIFICATION SYSTEM

TECHNICAL FIELD

This invention relates to methods and compositions useful in the rapid and efficient identification of fungal pathogens. The methods and compositions disclosed in the present invention utilize the differential morphologic and nutritive features of the genera and species of pathogenic fungi sought to be identified. In one aspect of the present invention, fungal pathogens are differentially identified by methods utilizing an improved formulation of a medium comprising a mixture of purified saponin, oxgall, a substrate for phenol oxidase, a supporting agent, and an ammonium salt. In another aspect, rapid and differential identification of fungal pathogens is provided by an improved method of carbohydrate assimilation, the improvement comprising preincubation of said fungal pathogens in a carbohydrate depleted medium prior to the plating of said fungal pathogens on culture plates containing a carbohydrate assimilation medium. In another aspect, methods utilizing miniaturized culture plates, for example having the dimensions of 33×75×5 millimeters, capable of differentiating fungal pathogens on five to fifteen fold less amount of fungal growth media than required by standard culture plates, are described. In a further aspect of the present invention, methods employing surface inoculation procedures are described which achieve a greater surface area to volume ratio than conventional techniques. In yet another aspect of the present invention, methods utilizing a single miniaturized culture plate containing either a combination of various fungal growth media or a number of different fungal pathogens, or both, are described. In still a further aspect, the improved fungal growth media, the improved carbohydrate assimilation method, and the methods utilizing miniaturized culture plates alone, and in combination, provide especially rapid and reliable techniques for the detection and differentiation of three clinically important fungi: *Candida albicans*, *Candida stellatoidea* and *Cryptococcus neoformans*.

BACKGROUND ART

Fungal pathogens vary in their pathogenicity, that is, their capacity to cause disease. At one end of the spectrum, highly pathogenic fungi may produce systemic disease when they infect. At the other end of the spectrum, some fungi may establish a more or less permanent residence on, and even in, the superficial body tissue. These fungi are unable to penetrate the body's natural defenses unless these defenses are seriously impaired. Such opportunistic infections have become more common as a byproduct of therapeutic advances and currently pose a significant medical threat to certain classes of individuals or patients. For example, patients receiving antibiotic therapy, undergoing surgical procedures, manipulation of indwelling catheters and those with altered host defense mechanisms due to the use of antibiotics, immunosuppressive drugs or radiation therapy have an increased risk of opportunistic fungal infection. Fungal infections in these already compromised individuals may result in life threatening disease.

Two of the most medically important types of fungi are *Candida albicans* and *Cryptococcus neoformans*. *Candida albicans* is an example of a relatively non-pathogenic yeast (that is, single cell fungus) that is frequently present on normal mucus membranes of the mouth and intestinal tract. *Candida albicans* generally will not establish an infection in healthy humans but can cause opportunistic infections resulting in chronic local infections in those with compromised host defense mechanisms. *Cryptococcus neoformans* is especially important because of its predilection for the central nervous system which can cause severe disease in biologically defenseless patients.

The presumptive identification of *Candida albicans* depends solely upon morphological changes which occur when this fungus is plated and allowed to grow on an appropriate medium. The first morphological change indicative of the presence of *Candida albicans* is the formation of germ tubes, which appear as tiny appendages extending from the plated unicellular specimens. These germ tubes eventually grow into elongated filaments extending outwardly from a body of the *Candida albicans*. Formation of germ tubes within 2 to 3 hours after plating of the fungus is presumptive evidence that *Candida albicans* or *Candida stellatoidea* are present. In a second stage of growth, generally round bodies appear at the ends of the filaments. These round bodies are known as chlamydospores. Only three species of the *Candida* genus will form chlamydospores. These are *Candida albicans*, *Candida stellatoidea*, and *Candida tropicalis*. Thus, chlamydospore formation is indicative of the presence of *Candida albicans*, *Candida stellatoidea*, or *Candida tropicalis*.

The differential identification of *Candida albicans* and *Candida stellatoidea* is made by a subsequent carbohydrate assimilation test. The basic concept for these tests includes a series of differential media which contain one specific carbohydrate, a nitrogen source and a color dye such as bromcresol purple which is pH sensitive. For yeasts, carbohydrate assimilation is an acidic reaction which can be monitored with pH-indicating dyes, while fermentation involves acid and gas production, requiring a pH-indicating dye and gas trap.

There are two methods presently used for assimilation: (1) a modified Wickerham method and (2) an auxanographic method. In general, the modified Wickerham method uses test tubes of carbohydrate agar media which contain a pH sensitive dye. The tubes are inoculated directly from a yeast subculture plated on a growth medium such as Sabouraud's dextrose agar by transferring a loop of organism to the surface of the carbohydrate agar. Positive assimilation reactions are noticeable in one to seven days. A conventional example of this method includes the inoculation of a test tube of sucrose media containing bromcresol purple with yeast followed by an examination at 24 to 72 hours for a color change of the medium from purple to yellow indicating sucrose assimilation. *Candida albicans* will give a positive assimilation while *Candida stellatoidea* is negative. The basic disadvantages are a long time-to-positivity and cumbersome and large storage space requiring specialized racks for storage.

Another conventional plate also utilizes the modified Wickerham method with one basic alteration. The plate is composed of a series of wedges arranged in a circular configuration which contain a carbohydrate media with bromcresol purple, an urea agar and a nitrate media. Instead of a direct inoculum transfer, the yeast is first suspended in sterile water and then transferred by sterile pipet to the various media. The plate is then incu-} bated and examined at 24 hours to 6 days for positive reactions. Disadvantages of this system are long time-to-positivity, relative expense and an increased amount of media used, each well requiring about ten milliliters of media.

The auxanographic method involves a pour plate technique where the yeast is suspended into molten carbohydrate agar medium. The yeast suspension is then poured into a sterile culture (hereinafter sometimes referred to as "petri") plate and allowed to solidify. There are two variations of this method. In one method, the medium does not contain carbohydrate, and after solidification, sterile paper discs impregnated with a specific carbohydrate are placed onto the agar surface of the inoculated pour plate. The carbohydrate then diffuses from the disc into the inoculated medium. Positive assimilation is then measured either by a pH change around the disc in the presence of a pH sensitive dye or by a ring of turbidity forming around the paper disc indicating the ability of the yeast to assimilate, or to grow on, that particular carbohydrate source. Sterile carbohydrate discs are available which can be incorporated into an identification system. With this system, eight or twelve different carbohydrate discs can be delivered in one application to a standard 100×15 mm petri plate of inoculated yeast assimilation medium. The disadvantages of this method are the necessity of a boiling bath to melt the agar medium, prolonged technician time, cumbersome storage, and the long time-to-positivity. Additionally, the temperature of the molten agar is typically between 40° and 45° C. at the time of yeast suspension in said agar. Temperatures above these temperatures can kill yeast cultures and thus produce false negatives in the assimilation test results.

Another approach to the auxanographic method is illustrated by the A.P.I. 20C System. In this system, a series of twenty wells containing lyophilized carbohydrates and a glass vial filled with the basic yeast assimilation medium, without a pH sensitive dye, is provided. The glass vial is placed in a boiling water bath to melt the agar medium. After cooling, the yeast is transferred to the medium using a sterile wooden applicator stick and the medium is stirred to make a uniform suspension. This suspension, is then transferred by sterile pipet to the nineteen carbohydrate wells and one negative growth control well and allowed to solidify. The inoculated strip of wells is then placed in a plastic incubation tray provided by A.P.I. and incubated at 30° C. This system requires reactions to be read at 24, 48 and 72 hours with a positive reaction determined by increasing turbidity. Disadvantages of this system are the necessity of a boiling water bath to melt the agar medium, technician time, long time-to-positivity, and relative expense. Additionally, the temperature of the melted agar is typically between 40° and 45° C. at the time of yeast suspension in said agar. Temperatures above these temperatures can kill yeast cultures and thus produce false negatives in the test results.

Identification of *Cryptococcus neoformans* is generally recognized to be more difficult than the identification of *Candida albicans* in that *Cryptococcus neoformans* undergoes no morphological changes which can be observed and remains unicellular throughout its growth cycle. Until recently, one or more of three basic tests, or a combination thereof, were employed to identify the presence of the genus Cryptococcus. One of the methods of identification comprises microscopic inspection of a specimen to identify whether or not a capsule-like formation around the cells of the fungi is present. In order to aid in the inspection of such capsule-like formations, a specimen is surrounded with india ink which enhances the appearance of the capsule by providing a clear and translucent image against the black background making such capsules easier to identify during microscopic examination. A second method employed to identify the genus Cryptococcus comprises plating the specimen on a medium containing urea and a color indicator. Because Cryptococcus produces an enzyme known as urease it has the capability to break down and use the nitrogen contained in the urea, causing the pH to rise, thereby changing the color of the indicator. Therefore, metabolism of a urea containing medium is indicative of the presence of *Cryptococcus, Trichosporon beigelii* or *Candida krusei*. A third method of identification of the genus Cryptococcus relies on the ability of that genus to produce a starch-like compound. When the starch-like compound is present, addition of iodine will cause a purple ring to appear around the colony. It is to be noted that none of these tests is specific for *Cryptococcus neoformans* by itself or in combination, as other species within the genus Cryptococcus and other genera of yeast may also give a positive reaction.

Although the urease test, described above, is not specific for *Cryptococcus neoformans*, it is a relatively rapid preliminary screen or the genus Cryptococcus which characteristically possess the enzyme urease that is necessary for the hydrolysis of urea. Three methods are currently employed to detect urease production by yeast cultures: (1) urea agar slant, (2) urea broth and (3) urease swab test. The urea agar slants are prepared from commercially dehydrated medium containing a color indicator. After autoclaving, slanting and solidification, the tubes are ready to use. Positive urease reactions are noted by a color change of the medium from orange to pink which occurs within 24 to 72 hours. The primary disadvantages are long time-to-positivity and technician time.

The urea broth test essentially changes the test to a liquid state and increases the inoculum to substrate ratio. The urea broth can be purchased commercially in a lyophilized form and must therefore be reconstituted prior to use. This test requires 3 to 4 hours for positive reactions incicated by a color change of the broth from orange to pink. Tne major disadvantages are preparation time and desirability of an even more rapid preliminary screen.

The urea swabs are prepared by impregnating sterile cotton applicator swabs with concentrated urea agar base, quick-freezing at −70° C. and lyophilizing overnight. The swabs are inoculated with 2 to 3 yeast colonies, placed into a test medium, the pH of the media is adjusted to pH 4.6, then incubated and examined for a positive reaction indicated by a color change which occurs within 15 to 20 minutes. The basic problem with this test is that the swabs are not commercially available and the pH adjustment for the swab is so critical that there is a likelihood of false negative or false positive reactions occuring.

Perhaps the single most successful and specific conventional test for *Cryptococcus neoformans* includes the use of bird seed agar. It was discovered that when *Cryptococcus neoformans* was present in a sample plated on bird seed agar a specific tell-tale brown color would appear, within a period of five days to two weeks. Tnis method was improved by using an extract of bird seed which lowered the identification time 3 to 5 days. Later it was discovered that the brown pigment coloration of the yeast was the result of the reaction between the enzyme phenol oxidase and a particular substrate present in bird seed agar. Accordingly, use of substituted phenols such as caffeic acid in the growth medium further shortened the period of time necessary for identification to about forty-eight hours. A still further refinement of the use of caffeic acid to identify *Cryptococcus neoformans* is set forth in an article by Hopfer and Groschel entitled "Six Hour Pigmentation Tests for the Identification of *Cryptococcus neoformans*", Journal of Clinical Microbiology, August 1975, Vol. II, No. 2, p. 96–98. The improvement set forth therein includes combining caffeic acid with ferric citrate and incorporating these compounds onto paper discs for use as substrates for the phenol oxidase enzyme activity of *Cryptococcus neoformans*. Use of these caffeic acid-ferric citrate impregnated paper discs further lowers the identification time to 3 to 6 hours. However, the solution of caffeic acid and ferric citrate used to impregnate the paper discs is quite unstable when exposed to light and temperature and therefore presents serious storage problems. These discs must be stored at −20° C. Furthermore, the relative concentration of caffeic acid and ferric citrate are critical and an unbalanced combination will require longer incubation periods for production of a dark pigment, or, in some cases, nonspecific pigmentation of saprophytic Cryptococcus and several Candida species. In an article entitled "Two Rapid Pigmentation Tests for Identification of *Cryptococcus neoformans*," Journal of Clinical Microbiology, February, 1982, Vol. 15, No. 2, p. 339–341, by Kaufmann and Merz, the authors present two tests for *Cryptococcus neoformans* based in part upon modifications of previous approaches to detect phenol oxidase activity. The first test employs corn meal agar containing an emulsifying agent sold under the tradename Tween 80 by Atlas Chemical Company supplemented with caffeic acid. The second is a non-medium test utilizing a phenol oxidase detection strip saturated with buffered L-$\beta$-3,4-dihydroxyphenylalanine (L-DOPA)-ferric citrate solution. While substrate stability is increased in these tests, storage still presents some problems as ferric citrate, for example, must be stored at −20° C.

Recently, a new culture medium for the identification of *Cryptococcus neoformans*, *Candida albicans* and *Candida stellatoidea* was discovered which includes caffeic acid, oxgall, saponin and a supporting agent. This medium (hereinafter sometimes referred to as original SOC) is disclosed in U.S. Pat. No. 4,144,133, issued Mar. 13, 1979 and entitled "Fungal Growth Media". The phenol oxidase substrate, preferably in the form of caffeic acid, provides for a specific identification of *Cryptococcus neoformans* by means of the appearance of the characteristic brown pigmentation of the yeast which results from specific enzyme activity of *Cryptococcus neoformans* on the phenol oxidase substrate. The oxgall, in addition to its known function of suppressing bacterial growth, has also been discovered to enhance filament and chlamydospore production of the medically important fungi *Candida albicans* and *Candida stellatoidea*. The purified saponin employed in the fungal media significantly enhances the germ tube and chlamydospore formation of *Candida albicans* thus providing for rapid identification of these especially serious types of pathogenic fungi. The carrying agent, such as common agar or silica gels for example, simply provides a supporting base for the above described active ingredients.

Although the SOC culture media are specific for identification of *Cryptococcus neoformans* and rapidly indicate the presence of either the *albicans* or *stellatoidea* species of the genus Candida, chlamydospore formation is weak in some strains of *Candida albicans* requiring 48 to 72 hours for formation rather than 28 to 48 hours for the strong chlamydospore formers.

Thus, while a variety of methods and media have been employed in order to identify and differentiate various fungal pathogens including the critically important genera and species *Candida albicans* and *Cryptococcus neoformans*, there is a continuing need for a fungal growth media and system which will rapidly identify and differentiate these genera and species as well as other pathogenic fungi in a rapid, efficacious, economic and technically efficient manner.

SUMMARY OF THE INVENTION

The present invention provides a miniaturized yeast identification system which allows for the rapid and reliable identification of the most commonly encountered opportunistic fungi infecting patients with compromised body defenses. Existing and improved differential fungal growth media are modified or adapted to miniature culture containers having dimensions such that it will fit on the viewing stand of a conventional microscope, for example a size of approximately $33 \times 75 \times 5$ millimeters. Preferably flip-up lid is pivotally attached to the sidewalls which when in the lowered or closed position will enclose the media within the container, but when pivotally open will allow easy addition, removal and inspection of the samples. These miniature plates have a physical form which is convenient for storage, examination and easily maintained sterility. The miniature configuration also affects the performance of various differential growth media. Specifically, the larger surface area to volume in the miniature plate allows rapid heat transfer between the incubation environment and the medium thus providing an enhanced temperature control essential with the SOC medium, and provides an easily attainable high organism to substrate ratio required by the carbohydrate assimilation and urea containing media, for example, from about $10^5$ to about $10^{12}$ organisms per about 0.2 centimeters squared to about 5 centimeters squared media. The present invention additionally provides an improved SOC medium, the improvement comprising the addition of ammonium ions. The addition of ammonium ions enhances chlamydospore formations in previously weak chlamydospore forming strains of *Candida albicans*. Additionally, this improved SOC medium has been further modified by increasing the concentration of the phenol oxidase substrate, caffeic acid, to allow for the adaptation of the SOC medium to the miniaturized system. The methods of the present invention further describe the use or these miniature plates so as to accommodate one or more organisms, one or more differential growth media, or a combination thereof to provide a compact and rapid yeast identification system.

BRIEF DESCRIPTION OF THE DRAWINGS

One aspect of the present invention, the novel miniature culture container, has dimensions such that it will fit on the viewing stand of a conventional microscope, for example, a size of approximately $33 \times 75 \times 5$ millimeters. The several embodiments of the novel containers can be more easily understood from a study of the drawings in which:

FIGS. 1-4 are perspective views of four distinct embodiments of the novel miniature culture container.

FIG. 5 is an enlarged fragmentary cross-sectional view of the structure of FIG. 1.

FIGS. 6-11 are perspective views of six distinct embodiments of the novel miniature culture container.

FIG. 12 is an enlarged fragmentary cross-sectional view of FIG. 10 taken along lines 12—12.

DETAILED DESCRIPTION

Figure 13:
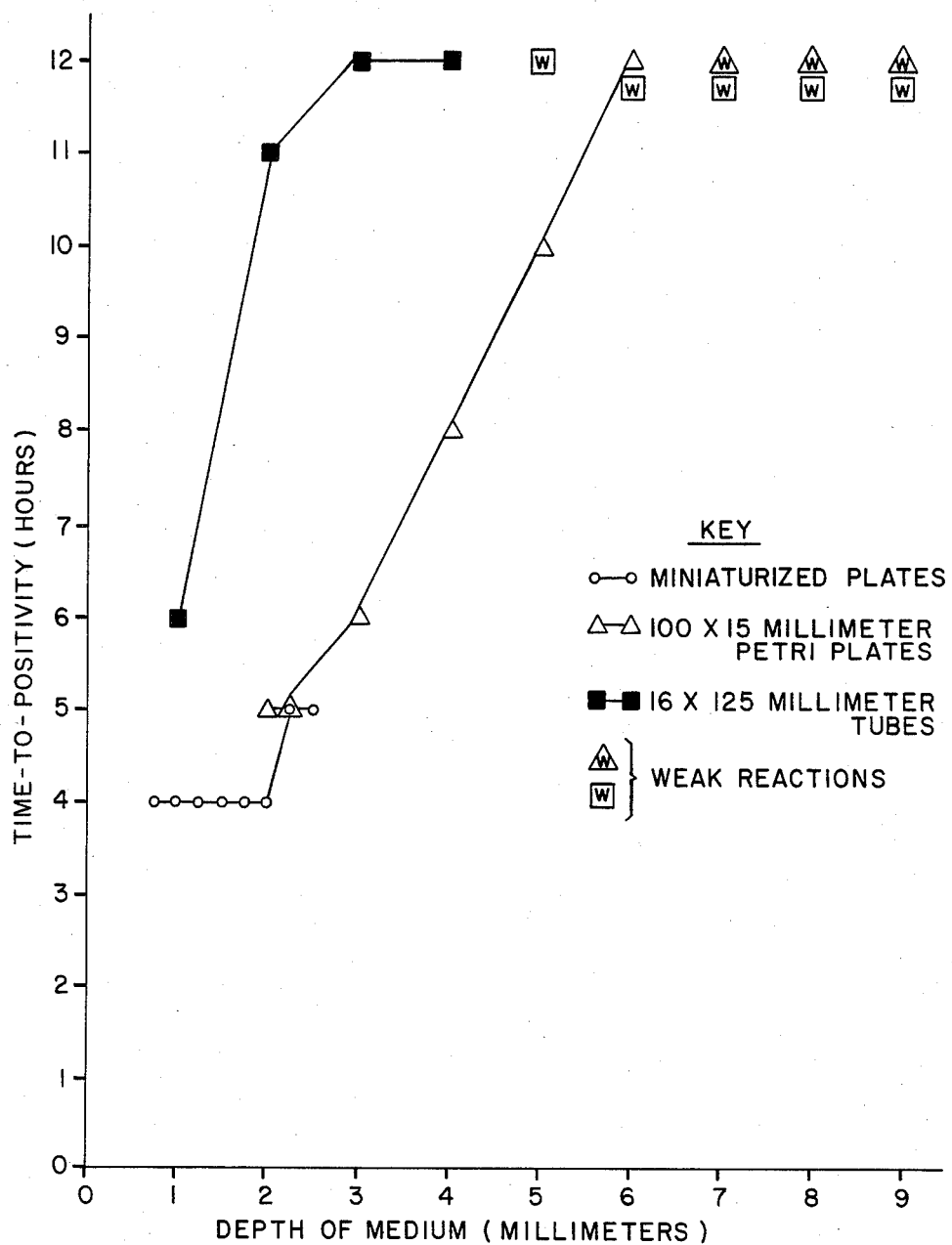
FIG. 13 is a graph showing the effect of fungal medium depth on the time-to-positivity in the carbohydrate assimilation test of Example 7.

The present invention relates to methods and compositions useful in the rapid and efficient identification of fungal pathogens.

In the context of this disclosure, the following terms shall be defined as follows unless otherwise stated:

"blastospore" is a spore formed by budding as in yeast (syn: yeast, yeast cell);

"chlamydospore" is a thick-walled, non-deciduous asexual spore made by the rounding up of a cell either intercalary (at the junction of two cells in a filament) or terminally (at the end of a filament);

"filament" is a thread-like series of elongated yeast cells;

"germ tube" is a hyphal extension from a yeast cell which has no constriction or cell wall at the point of production;

"pseudohypha" is a hyphal extension from a yeast cell formed by the elongation of a budding cell where constriction and cell walls separate one yeast cell from the other;

"pseudomycelium" is a mass of filaments formed by elongated yeast cells;

"yeast" is a unicellular, budding fungus.

The miniaturized yeast identification system of the present invention provides an especially rapid, reliable, economic and technically efficient method for the differentiation of most medically important types of potentially pathogenic fungi.

The yeast identification system contains at least one differential medium which is provided in a miniature culture plate described in more detail below. The media include an improved fungal growth medium, the improvement comprising the addition of ammonium ions to a medium comprising purified saponin, oxgall, a substrate for phenol oxidase and a supporting agent (hereinafter sometimes referred to as SOC), carbohydrate assimilation media and a urease medium. The miniature media containing plates may be constructed to contain a single medium, as shown in FIGS. 1 through 4, or may be partitioned, as shown by example in FIGS. 6 through 11. It is envisioned that plates may be so partitioned to accommodate as many as twenty different media.

Generally, saponins may be purified using the techniques set forth in U.S. Pat. No 3,883,425 entitled "DETOXIFICATION OF SAPONINS", issued May 13, 1975, incorporated by reference herein, and the purified saponins can then be employed in the fungal medium of the present invention. The use and adaptation of these media to miniature culture plates significantly enhances the performance of these media in differentially identifying various genera and species of clinically important fungi. The miniaturized yeast identification system of the present invention also includes a modification of the carbohydrate assimilation test, said modification comprising the preincubation of the fungi in a carbohydrate depleted medium prior to plating on a carbohydrate assimilation media. The described modification significantly decreases the time-to-positivity, specifically, from 24 to between four and six hours for some species. The use and adaptation of these media to the miniaturized system provides both a surface inoculation method and greater surface area to volume ratio than conventional methods which can reduce the number of false negative identifications that may occur when pour plate methods are used. This miniaturization also has economic and mechanical advantages. The miniaturized yeast identification system of the present invention is particularly useful in the differential identification *Cryptococcus neoformans, Candida albicans* and *Candida stellatoidea.*

The miniature plate has dimensions such that it will fit on the viewing stand of a conventional microscope, for example of from about 0.03 to about 3 centimeters by from about 0.7 to about 8 centimeters with a depth of from about 0.025 centimeters to about 1.0 centimeters. The preferred size is approximately 35×75×5 millimeters, embodiments 10 and 20 in FIGS. 1 and 2 respectively, and has a flip-up lid 12 which is pivotally attached to the sidewalls 14a and 14b and which when in the lowered position, see FIG. 5, will enclose the media 16 within the plate 18 but when pivotally open, see FIG. 1, will allow easy addition, removal and inspection of the samples. The standard petri plate is a circular plate with the approximate dimensions of 100×15 millimeters and has a non-attached lid which fits over the bottom, media containing, plate. The miniaturized configuration has several advantages. Specifically, these advantages include ease of packaging and storage, requiring little refrigeration room, and increased facility in maintaining sterility as the plates are easily handled and stacked without the fear of knocking off the lid which is a common occurrence with conventional petri plates. Additionally, with the morphology medium SOC, the miniature plate configuration fits the microscope stage slide holder allowing rapid manipulation of the plates as opposed to the slow, awkward manipulation of standard petri plates by hand and by eliminating the need to transfer the yeast specimen to a second microscope slide for examination.

Referring to the drawings, FIGS. 1, 2, 8, 9, 10 and 11 represent rectangular embodiments of the miniature culture plate of the present invention. As shown by example in FIGS. 1 and 2, these embodiments may possess a flip-up lid 12 which is pivotally attached to side walls 14a and 14b may possess an unattached lid 22. Both lids 12 and 22 may be lowered upon plates 18 and 28, respestively, to enclose the media 16 contained within plates 18, 28, 50, 54, 60 and 70 in a manner best shown in FIG. 5. As shown by example in FIGS. 8 through 11, the rectangular plates 18 and 28 of embodiments 10 and 20, respectively, may be partitioned in such a manner as to create circular wells 62a, 62b, 72a-h, shown in detail in FIG. 12, square wells 55a-h, or rectangular wells 52a-c, and 64a-b or a combination thereof as shown in embodiment 60. Alternatively, the miniature culture plates may be circular in configuration as shown by embodiments 30 and 40 in FIGS. 3 and 4, respectively. The circular plates 38, 48, 80 and 90 may similarly possess a flip-up lid 32 which is pivotally attached to the circumferential sidewall 34 or may possess an unattached lid 42, both of which enclose the media 16 contained within plates 38, 48, 80, and 90 when the lids 32 and 42 are lowered upon the circumferential sidewalls 34 and 44, respectively. In a manner similar to the rectangular plates 18, 28, 50, 54, 60 and 70, the circular plates 38, 48, 80 and 90 may be partitioned as shown in FIGS. 6 and 7 to create wells of such shapes as circles 92a and 92b or triangular pie-shaped wells 82a–f and 94a–d or any combination thereof, for example embodiment 90, FIG. 7. The shape of the miniature culture plate and media containing wells therein, shown in FIGS. 1 through 12. are set forth as examples and are not meant to limit the types of possible shapes and combinations thereof employed. The miniature culture plate may be constructed of plastic or such material presently employed in the manufacture of petri plates.

The miniature plates are more economical in that they utilize between about 2.5 to 5 milliliters of media as opposed to the about 20 to 30 milliliters of media required by the standard petri plates. The miniaturized yeast identification system has been designed to utilize a slide warmer as an alternative mini-incubator. One such slide warmer is commercially available from Fisher Scientific Company. There are two requirements for use of slide warmers: (1) an adjustable thermostat which can be set at 37° C. and (2) a cover or lid for the warming surface. Both the purchase cost and space needs of a slide warmer are considerably less than a conventional incubator.

The miniaturized yeast identification system of the present invention provides pre-poured, sterilized, ready to use media and thereby circumvents the disadvantages of existing systems, such as the auxanographic carbohydrate assimilation method which necessitates such steps as boiling, to dissolve the agar supporting agent and sterilization prior to use. A conventional product with a ready-to-use agar for chlamydospore production uses corn meal agar with an emulsifying agent sold under the tradename Tween 80 by Atlas Chemical Company and accompanies media for urea, nitrate and carbohydrate utilization. The corn meal agar is inoculated and examined at 24 to 72 hours for chlamydospore production. The two main disadvantages of this system are that the chlamydospore tests cannot be performed apart from utilizing the entire plate which is relatively expensive and there is a long time-to-positivity.

In the miniaturized yeast identification system of the present invention, the media are prepared, poured into the miniature plates and after solidification, the lids are closed, and the plates are wrapped in a plastic lined aluminum pouch. These plates may be stored up to at least 8 months at 4° C. without loss of differential growth capabilities.

The miniature configuration also affects the performance of the media. Temperature control is essential with these media and the smaller volume of media in the miniature plate allows rapid heat transfer between incubation environment and the medium. The sensitivity and accuracy of short term incubations, such as the three hour, 37° C. incubation for germ tube formation and subsequent shift to room temperature for chlamydospore production on the SOC medium, are significantly enhanced by the miniaturization of the system. The performance of the sucrose assimilation and urease tests is also enhanced. Both of the latter tests require a very high organism to substrate ratio which is easily attainable in the small media volume of the miniature plate. Additionally, both tests involve a color change of the media which is more easily visualized with a medium depth of about 1 to 4.5 millimeters han at about 5 to 15 millimeters. This increased organism to substrate ratio and more easily visualized color change are thought to be partially responsible for the decreased time-to-positivity of the sucrose and urease tests in the miniaturized system of the present invention, the times being 5 and 1 hours, respectively.

Use of the SOC media in the miniaturized system of the present invention requires a modification in the concentration of the phenol oxidase substrate. The preferred substrate is caffeic acid, however, some other suitable substrate of phenol oxidase enzymes may be employed. Suitable pnenol oxidase substrates include 2,3-dihydroxybenzoic acid, 3,4dihydroxybenzoic acid (protocatechuic acid), DOPA, 3,4-dihydroxycinnamic acid (caffeic acid), the methyl ester and diacetate of caffeic acid, 3-hydroxytryptamine, 3,4-dihydroxyphenylethanolamine (norepinephrine), and 4-hydroxy-3,5-dimethoxycinnamic acid. The substrate of phenol oxidase is employed as an identification agent for *Cryptococcus neoformans* since the reaction of the phenol oxidase enzyme of that fungus with such a substrate produces a brownish pigmentation of the organism which is specific for *Cryptococcus neoformans*. The original SOC formulation, as given in U.S. Pat. No. 4,144,133, issued Mar. 13, 1979 and entitled "FUNGAL GROWTH MEDIA", was from about 0.005 to about 0.05 weight percent caffeic acid. Adaptation of the original SOC media to the miniaturized system requires an increased range of about 0.005 to about 0.5 weight percent, with a preferred concentration of about 0.012 to about 0.12 weight percent and a most preferred concentration of about 0.06 weight percent caffeic acid. This higher concentration of caffeic acid necessitates an upward adjustment of the pH of the medium to a neutral pH due to the acidic nature of caffeic acid.

It was noted that chlamydospore formation, in certain strains of *Candida albicans*, was very weak on the original SOC media, requiring a 48 to 72 hour incubation for production. Publications by McClary, *Annals Missouri Bot. Gar.*, 39:137–164 (1952) and Nickerson, *Internat'l. Congress of Microbiol. Report Proceedings*, 5th Congress, Rio de Janeiro, p. 130–131 (1950), indicated that low concentrations of ammonium sulfate or ammonium chloride support filamentation in Candida species. Other work by Jansons, et al., *J. Bacteriol*, 104, 2:910–921 (1970); Land, et al., *Infect. and Immun.*, 11, 5:1014–1023 (1975); Mardon, et al., *J. Bacteriol*, 100:701–707 (1969); and Nickerson, ibid, stated that ammonium salts support yeast growth. Twenty strains of *Candida albicans* were chosen, which on occasion had given negative or weak chlamydospore formation, and were tested for germ tube and chlamydospore formation on SOC media containing a range of ammonium ion concentrations in the miniaturized system. All twenty strains produced numerous germ tubes on ammonium ion containing SOC media after three hours at 37° C. The concentration range of ammonium ions, added in the form of ammonium salts, supporting chlamydospore formation was found to be between about 0.001 M and about 0.5 M with a preferred concentration of about 0.005 M to about 0.05 M and a most preferred concentration of ammonium salt at about 0.01 M. Ammonium salts may be selected from a non-exclusive class comprising, ammonium chloride, ammonium sulfate, ammonium nitrate and ammonium citrate, of which the preferred ammonium salt is ammonium chloride. Other salts such as sodium chloride and potassium chloride were tested by formulation in the SOC media but were found to be less effective in promoting chlamydospore formation than the ammonium salts.

Miniaturization of the SOC medium also required an increase in the preferred concentration of purified saponin from the original concentration of about 0.5 weight percent to about 1.0 weight percent in the improved SOC medium of the present invention.

The SOC medium used in the miniaturized yeast identification system was prepared by adding a powdered supporting agent such as agar, oxgall, purified saponin, a substance for phenor oxidase such as caffeic acid, and ammonium salt to deionized water. The resulting mixture was then stirred and heated to boiling to dissolve the ingredients and adjusted to a final pH of about 6.5 to about 7.5. The solution was then sterilized at 121° C. at about 15 psi for 15 minutes. After cooling, the medium was dispensed to a depth of about 2 millimeters into 33×75×5 mm rectangular plastic plates with attached flip-up lids. The medium was allowed to solidify, and the plates were wrapped in plastic lined aluminum foil pouches and stored at 4° C. Preparation and storage in this fashion gives a shelf life of at least 8 months.

Generally, the improved SOC medium of the present invention comprises from about 1.0 to about 5.0 weight percent agar, from about 0.25 to about 30.0 weight percent oxgall, from about 0.1 to about 5.0 weight percent purified saponin, from about 0.005 to about 0.5 weight percent caffeic acid, based on the amount of water added to these components and from about 0.001 M to about 0.5 M ammonium salts.

Preferred media can be prepared following the procedure outlined above and employing from about 1.0 to about 5.0 weight percent agar, from about 0.5 to about 5.0 weight percent oxgall, from about 0.1 to about 2.5 weight percent purified saponin, from about 0.012 to about 0.12 weight percent caffeic acid, and from about 0.005 M to about 0.05 M ammonium salts. A most preferred medium contains about 2.0 weight percent agar, about 1.0 weight percent oxgall, about 1.0 weight percent purified saponin, about 0.06 weight percent caffeic acid, and about 0.01 M ammonium salts.

Prior to inoculation of the miniature SOC media-containing plates with the yeast samples, the yeasts are grown on a general growth medium, such as Sabouraud dextrose agar with gentamicin, for up to about 72 hours. Anywhere from about one to three yeast colonies may be taken from the general growth medium and plated on each miniature plate. All yeasts were first grown on a general growth media prior to inoculation of media-containing miniature plates. These general growth media may contain antibiotics.

The miniaturized yeast identification system of the present invention has also been adapted to accommodate carbohydrate assimilation media. Adaptation of these assimilation media to the miniaturized system allows clinical technicians to selectively choose those assimilations required for a specific speciation of potential pathogenic fungi and thereby shortens the time of species identification from one week to about five to twenty four hours. Sucrose assimilation, for example, specifically differentiates *Candida albicans*, which assimilates sucrose, from *Candida stellatoidea*, which does not. When used in conjunction with such morphology tests as germ tube and chlamydospore formation, which gives a presumptive identification of the *albicans* or *stellatoidea* species, the conducting of sucrose assimilation tests will give a conclusive species identification. Additionally, adaptation of such carbohydrate assimilation media as sucrose has dramatically shortened the time-to-positivity for *Candida albicans* and *Candida stellatoidea* differentiation.

The method of the present invention shortens the time-to-positivity for sucrose assimilation from 24 hours, and in some tests 6 days, to a period of about 5 hours. This increased efficiency is believed to be due to at least two novel features of the present invention. First, the procedure employed for sucrose assimilation utilizes a starvation step, in a carbohydrate depleted media, prior to plating of the fungi on the assimilation media. The purpose of this prestarvation step is to deplete the yeast cells of essentially all of the internal carbohydrate pools which prevents false positive reactions. This prestarvation is believed to increase the rate of carbohydrate assimilation once the yeasts are plated on carbohydrate containing media and thus decrease the time-to-positivity. Second, the miniature plates have a media depth of about 1 millimeter to about 4.5 millimeters as opposed to 5 millimeters to 15 millimeters in the standard petri plate. The shallower depth of the miniature plates is thought to aid in a more rapid visualization of the color change resulting from positive carbohydrate assimilation and to provide the essential high organism to substrate ratio.

In the miniaturized yeast assimilation system, a sucrose assimilation is utilized to differentiate between *Candida albicans* and *Candida stellatoidea*. The medium was prepared by adding a powdered supporting agent, such as agar, a pH sensitive color dye, such as bromcresol purple, and a yeast nitrogen base to deionized water. The resulting mixture is then stirred, heated to boiling to dissolve the media components and adjusted to a pH of about 6.85 to about 7.55 with a base, such as sodium hydroxide. The medium is then sterilized by heating to 121° C. at 15 psi for 15 minutes. The sucrose is presterilized and then added asceptically to the medium mixture. The cooled sucrose-containing medium is then dispensed in about 5 milliliter aliquots into sterile rectangular plates with attached flip-up lids, the plates having the approximate dimensions of 33×75×5 millimeters. After solidification, the lids are closed, and the plates wrapped in plastic lined aluminum foil pouches and stored at 4° C. These plates may be stored up to at least 8 months at 4° C. without dehydration or loss of color. Other sugars, such as maltose, galactose, trehalose, and lactose, may be substituted for sucrose to provide additional carbohydrate assimilation media. These sugars are but non-exclusive examples of carbohydrates which may be substituted for sucrose in the above-described carbohydrate assimilation media. Additionally, it is envisioned that a series of different carbohydrate assimilations may be conducted simultaneously by utilizing containers such as those shown in FIGS. 6 through 11. Fluorescent indicators which show a definite change in fluorescence with change in pH may be substituted for the pH sensitive color dyes employed in the examples of the present invention. Fluorescent indicators operable in the pH range, pH 5 to pH 8, of the carbohydrate assimilation system include, for example, Acid R Phosphine, Brilliant Diazol Yellow, Cleves acid, Coumaric acid, 3,6-Dioxyphthalic dinitrile, Magnesium 8-hydroxyquinolinate, β-Methylumbelliferone, 1-Naphthol-4-sulfonic acid, Orcinaurine, Patent Phosphine, Thioflavine and Umbelliferone.

A preferred medium can be prepared following the procedure outlined above and employing from about one to about five weight percent agar, from about 0.0005 to about 0.02 weight percent bromcresol purple, from about 0.02 to about 0.7 weight percent yeast nitrogen base, and about 0.02 to about 1.0 percent sucrose, based on the amount of water added to these components. The preferred pH of the medium, prior to sterilization is about 6.85 to about 7.55.

Prior to inoculation of the assimilation media, the yeasts were taken from plates containing a general growth medium and suspended in sterile, carbohydrate depleted media at a pH of about 7.0 to about 8.5 and held at room temperature. Examples of carbohydrate depleted media include sterile, deionized water or deionized water supplemented with a yeast nitrogen base. The prestarvation period may run from about 30 minutes to 24 hours with a preferred range from about 30 minutes to about 8 hours, and a most preferred period of about one hour. Prestarvations were carried out in non-glass, sealed and sterile containers. Such prestarvation techniques have been employed in genetic and biochemical studies of microorganisms generally, but have not been previously employed in yeast assimilation methods for taxonomic purposes.

After prestarvation, the carbohydrate depleted medium containing the yeast is vigorously mixed and, thereafter, at least ten microliters of yeast suspension is placed onto the surface of the assimilation media. Multiple individual aliquots of yeast suspensions may be placed on each miniature plate. The plates are then incubated at room temperature for about 4 to 6 hours and thereafter checked for color change from purple to yellow denoting carbohydrate assimilation.

An alternative embodiment of the miniaturized yeast assimilation system has been developed which combines prestarvation of the yeast inocula with subsequent inoculation of the prestarved yeast onto a series of miniaturized carbohydrate agars, incubation of said inocula on said agars and post-incubation dye or fluorescent indicator addition for detection of carbohydrate assimilation.

In this alternative embodiment, the yeasts were again taken from plates containing a general yeast growth medium and suspended at a concentration of McFarland No. 8, approximately 108 organisms, in either the prestarvation media previously described or $1 \times 10^{-5}$ M NaOH. The prestarvation period may run from about 30 minutes to about 24 hours with a preferred range from about 30 minutes to about 8 hours, and a most preferred prestarvation incubation period of about one hour at a preferred temperature of about 20° to 25° C. Prestarvations are, again, performed in sterile, sealed, non-glass containers at the previously described pH.

Following prestarvation, the carbohydrate depleted medium containing the yeast is vigorously mixed and, thereafter, at least 10 microliters of yeast suspension is placed onto the surface of the assimilation medium.

The carbohydrate assimilation media employed in this alternative embodiment were prepared by suspending appropriate amounts of yeast nitrogen base and agar into deionized water. The resulting mixture was stirred with heat sufficient to dissolve the ingredients and the pH of the suspension was adjusted to about 7.2 with an allowable pH range of from about 6.65 to about 7.35. The mixture was then sterilized at 121° C. at 15 psi for 15 minutes, cooled to about 40° to 55° C. and, thereafter, an appropriate amount of filter-sterilized carbohydrate added aseptically. About 5 milliliter aliquots of this molten medium was then pipetted into sterile rectangular plates with attached flip-up lids, the plates having the approximate dimensions of $33 \times 75 \times 5$ millimeters. After solidification, the lids are closed and the plates wrapped in plastic lined aluminum foil pouches and stored at 4° C. These plates may be stored up to at least 8 months at 4° C. without dehydration. A nonexclusive list of the type of sugars which may be employed in this alternative embodiment includes dextrose, galactose, sucrose, maltose, cellibiose, trehalose, lactose, melibiose, and raffinose. In the event that a single yeast inoculum is to be simultaneously tested for its ability to assimilate many different carbohydrates, the miniaturized plates shown in FIGS. 6 through 11 may be employed. The individual wells such as $72a$ through $72h$ in FIG. 10 or compartments such as $55a$ through $55h$ in FIG. 9 will each contain a different carbohydrate-containing medium and at least 10 microliters of yeast suspension was distributed per individual well or compartment.

A preferred medium can be prepared following the procedure outlined above and employing from about 0.02 to about 0.7 weight percent yeast nitrogen base, from about 1.0 to about 5.0 weight percent agar, and from about 0.02 to about 1.0 weight percent carbohydrate, based on the amount of water added to these components. The preferred pH of the medium is from about 6.65 to about 7.35. A most preferred medium contains about 0.067 weight percent yeast nitrogen base, about 2.0 weight percent agar, and about 0.1 weight percent carbohydrate, based on the amount of water added to these components. The most preferred pH is about 7.2.

Following inoculation of the carbohydrate-containing medium with an appropriate aliquot of yeast suspension, the plates are then covered with a sterile lid and incubated at room temperature for about 6 to 24 hours. After incubatior, an appropriate amount of dye solution is added to each assimilation test plate and assimilation detected by color changes in the dye. Three dyes were examined for possible use in this system, bromcresol purple, chlorophenol red and p-nitrophenol which give a purple to yellow, red to yellow and a colorless to yellow color change, respectively, when carbohydrate assimilation occurs.

The dyes were prepared by dissolving an appropriate amount of dye into water, adjusting the pH of the dye solution to about 7.2 using 0.05 N NaOH, and filter-sterilizing the solution through a 0.22 $\mu$m filter. A broad concentration range of dye solutions, from about 20 micrograms to 250 micrograms bromcresol purple or chlorophenol red per milliliter or from about 15 micrograms to 45 micrograms p-nitrophenol per milliliter, may be employed as stock solutions from which an appropriate aliquot of dye is taken and added to the carbohydrate assimilation test plates. The preferred concentration for the stock dye solutions is about 40 micrograms bromcresol purple dye per milliliter, 60 mg chlorophenol red dye per milliliter and 20 micrograms p-nitrophenol dye per milliliter. The most preferred dye is bromcresol purple. Approximately 0.02 ml to about 1.0 ml stock dye solution is added per about 0.1 to about 5.0 milliliters of yeast inoculated carbohydrate assimilation test medium, respectively. The bromcresol purple reaction requires about 5 to 15 minutes for completion, whereas the chlorophenol red requires about 15 to 60 minutes for completion.

The miniaturized yeast identification system of the present invention has also been adapted to accommodate urea containing media. The Cryptococcus species, and occasional *Trichosporon beigelii*, and a very rare *Candida krusei* possess the enzyme, urease, that is necessary for hydrolysis of urea. Presence of the urease enzyme in yeast cultures is indicated by color change of the medium from orange to pink.

The adaptation of urea containing medium to the miniaturized system of the present invention provides a positive detection of the enzyme, urease, in about one hour as opposed to the 24 to 72 hours and 3 to 4 hours required for urease detection in presently available urea agar slants and urea broth, respectively. The shortened time-to-positivity of the present method is believed to be due to the increased organism to substrate ratio provided by the small media volume and increased relative surface area and by easier visualization of the color change afforded by the shallower media depth in the miniaturized system as compared to standard petri plates, agar slants, and broth tubes.

The miniature urease plates of the present invention are made by preparing urea agar in accordance with manufacturer's instructions. The medium was sterilized by heating to 121° C. at about 15 psi for 15 minutes and is then dispensed in about 5 milliliter aliquots into the miniature plates described above. After solidification, the plates were wrapped and stored as described above so as to remain stable for at least eight months when stored as described above. The plates were inoculated by transferring one to three yeast colonies from a general growth media onto the urease media. The plates were then allowed to incubate at 35° C. for one hour.

The media adapted for use in the miniaturized yeast identification system of the present invention may be employed alone or in combination. When employing the partitioned plates shown in FIGS. 6 through 11, each plate may, for example, contain a single type of medium inoculated with several different yeasts, or each plate may contain multiple, different differential media inoculated with the same or multiple yeasts.

The fungal media of the present invention alone and in combination provide a rapid screening process for the identification of clinically important yeasts. Specifically, the miniaturized yeast identification systems described herein provide for the relatively rapid differential identification of *Cryptococcus neoformans* and the two Candida species, *albicans* and *stellatoidea*. It is further understood that while this invention has been described in relation to its preferred embodiments, the various modifications thereof will not be apparent to one skilled in the art from reading this specification and it is intended to cover such modifications as fall within the scope of the appended claims.

EXAMPLES

The following examples demonstrate the mechanical advantages, increased accuracy and decreased time-to-positivity of the present invention over those previously employed for the identification of various fungi, including *Candida albicans, Candida stellatoidea* and *Cryptococcus neoformans*. These examples are submitted for the purpose of providing a better understanding of the present invention and are not to be construed as limiting the scope thereof.

EXAMPLE 1

This example was performed in order to compare the accuracy and sensitivity of egg white media, fetal bovine media, two commercial systems, Flow GBE and A.P.I. GT TM Microtest, respectively, and the miniaturized SOC media of the present invention in detecting germ tube formation. The ease of manipulation and microscopic examination of these media was also compared.

Stock yeast strains were subcultured onto Sabouraud dextrose agar and allowed to grow for up to 72 hours. The yeast colonies formed by growth of the stock yeast on the Sabouraud dextrose agar were used to inoculate the test media in this comparative study.

In both the egg white and serum media the substrate was added to a test tube, inoculated with yeast and incubated at 37° C. for 3 hours. Following incubation, a drop of yeast suspension was placed on a microscope slide, covered with a glass coverslip, and examined under the microscope at 100× to 400× magnification for germ tubes. Egg white substrate was prepared by separating the egg white from the yolk of an egg. Fetal bovine serum substrate was purchased from Gibco. The Flow GBE tube, containing 0.1 percent weight per volume glucose and 2.6 percent weight per volume beef extract was inoculated with yeast and incubated as per manufacturer's directions in a 35° to 37° C. incubator for 2 to 4 hours. After incubation, one drop of inoculated broth was placed on a microscope slide, covered with a glass coverslip, and examined under the microscope at 100X magnification for germ tubes. The A.P.I. GT TM Microtest, consisting of microtubes containing 70 microliters lyophilized rabbit plasma with EDTA, was prepared according to manufacturer's directions, inoculated with yeast and incubated, as per manufacturer's instructions, in a 35° to 37° C. incubator for 2 to 5 hours. After incubation, one drop of yeast suspension was placed on a microscope slide, covered with a coverslip and examined under the microscope at 400× magnification for the presence of germ tubes. The miniaturized SOC plates were prepared as previously described. One to four colonies of yeast are picked up with a sterile cotton swab and the bulk of the inoculum was deposited as a single mound onto the miniaturized SOC media. From the remaining inoculum on the swab, a thin film of yeast was streaked onto the medium in a dollar sign shape and the thin film of yeast thereafter covered with a glass coverslip. The lid of the miniaturized plate was closed, and the plate was incubated at 37° to 40° C. for 3 hours. Following incubation, the miniaturized plate was opened, placed under the microscope, and the inoculum, centrally located under the coverslip, was examined at 100X to 400X magnification for germ tubes.

Table 1 gives the comparative results on the performance of germ tube systems. Twenty strains of *Candida albicans* were tested for germ tube formation and ease of microscopic examination on egg white, fetal bovine serum, Flow GBE, A.P.I. GT TM Microtest and the miniaturized SOC medium of the present invention. Each strain was examined after three hours of incubation and marked as positive (+) for germ tube formation when at least eight out of ten microscopic fields showed germ tube formation. The strains were marked as marginal (±) when germ tubes were visible in only one or two out of ten microscopic fields. Clumping was said to occur when, despite agitation, the germinated cells remained knotted together in masses, making it difficult to observe, microscopically, whether there is true germ tube or pseudohyphal formation.

TABLE 1

COMPARISON OF THE MINIATURIZED SOC PLATE WITH OTHER AVAILABLE SYSTEMS FOR GERM TUBE FORMATION BY *Candida albicans*

| | | Germ Tube Formation | | | | | |
|---|---|---|---|---|---|---|---|
| | No. of | + | | ± | | Clumping | |
| System | Isolates | No. | % | No. | % | No. | % |
| 1. SOC | 20 | 20 | 100 | 0 | 0 | 0 | 0 |
| 2. Egg white | 20 | 20 | 100 | 0 | 0 | 0 | 0 |
| 3. Fetal bovine serum | 20 | 20 | 100 | 0 | 0 | 2 | 10 |
| 4. Flow GBE tube | 20 | 18 | 90 | 2 | 10 | 4 | 20 |
| 5. API GT Microtest | 20 | 17 | 85 | 3 | 15 | 16 | 80 |

As can be seen from a study of Table 1, 100 percent of the strains tested formed germ tubes in three hours on the miniaturized SOC, egg white and fetal bovine serum media, while only 90 percent and 85 percent of the strains formed germ tubes in the Flow GBE and A.P.I. GT TM Microtest system, respectively. As shown in the results displayed in Table 1, significant clumping was observed in the serum, Flow GBE and A.P.I. GT TM Microtest systems. The miniaturized SOC medium is a solid support medium on which yeast cells are dispersed in a thin film allowing observation of single stationary cells. In the other systems, the yeasts are usually in motion in the liquid under the coverslip, making it difficult to focus on any one cell.

From the standpoint of the manipulation, the miniaturized SOC plate requires only an initial inoculum transfer, whereas the other systems require a second transfer to a microscope slide which increases technician time and necessitates additional materials.

EXAMPLE 2

This example was performed in order to establish the effect of various concentrations of the phenol oxidase substrate, caffeic acid, on yeast morphology and pigment formation on SOC media in the miniaturized system. The specific morphologies observed were germ tube, chlamydospore, blastospore, filaments and pseudohyphae formation. The brown pigment production characteristic of several *Cryptococcus neoformans* strains was also monitored.

The test medium, the miniaturized SOC medium, of the present example was prepared as follows: 20 grams of agar, 10 grams of oxgall, 10 grams of purified saponin, 0.54 grams of ammonium chloride, and various amounts of caffeic acid, listed in Table 2 below, were added to one liter of deionized water. The mixture thus formed was stirred and heated to boiling to dissolve the ingredients and adjusted to a final pH of about 7.2. The solution is then sterilized by heating to about 121° C. at 15 psi for 15 minutes. After cooling, the medium was dispensed to a depth of about 2 millimeters (approximately 5 milliliters) into sterile, miniature plates, previously described, and allowed to solidify.

One to four yeast colonies were transferred from a general growth medium to the test medium, as described in Example 1. The inoculated plates were incubated for 3 hours at 37° C. and thereafter at room temperature.

Table 2 sets forth the results of the test performed in order to compare the effect of various concentrations of caffeic acid on yeast morphology and pigment production on the miniaturized SOC medium. Six species of Candida and four species of Cryptococcus were plated on the test medium and observed at the time interval specified in Table 2. Microscopic examination at the time intervals designated in Table 2 was conducted at 100× magnification in the manner described in Example 1. Positive morphology (+) was defined as at least 8 out of 10 microscopic fields having shown a particular morphology or combination of morphologies. Negative morphology (−) was defined as less than 1 or 2 out of 10 microscopic fields having shown a particular anticipated morphology or combination thereof.

As can be seen from Table 2 below, the miniaturized SOC media supported the characteristic yeast morphologies and pigment production at a relatively wide range of caffeic acid concentrations, from about 0.005 weight percent to about 0.5 weight percent. In pigment formation, 10 percent of the *Cryptococcus neoformans* strains tested produced brown coloration at 18 hours on SOC with 0.006 weight percent caffeic acid. At 0.6 weight percent, SOC itself was dark brown, making the yeast's color change difficult to recognize and, also, the SOC medium became a darker brown color each day, indicating instability. The effect of caffeic acid concentration on general yeast morphology, as shown in Table 2 below, establishes an upper limit for caffeic acid. Essentially all filamentation of Candida species was inhibited at 0.6 weight percent caffeic acid.

TABLE 2

MORPHOLOGY AND PIGMENT PRODUCTION ON MINIATURIZED SOC MEDIUM AT VARIOUS CONCENTRATIONS OF CAFFEIC ACID

| | | Weight Percent Caffeic Acid | | | |
|---|---|---|---|---|---|
| Organism | Incubation Time (hrs.) | 0.006 | 0.06 | 0.12 | 0.6 |
| *Candida albicans* | 3 | gt+ | gt+ | gt−+ | gt− |
| | 24 | fil +/cm+ | fil +/cm+ | fil +/cm+ | fil −/cm− |
| *Candida stellatoidea* | 3 | gt− | gt− | gt− | gt− |
| | 24 | fil +/cm− | fil +/cm− | fil +/cm− | fil −/cm− |
| *Candida tropicalis* | 3 | ps+ | ps+ | ps− | ps− |
| | 24 | fil+ | fil+ | fil+ | fil− |
| *Candida krusei* | 3 | b+ | b+ | b+ | b+ |
| | 24 | fil+ | fil+ | fil+ | fil− |
| *Candida guilliermondii* | 3 | b+ | b+ | b+ | b+ |
| | 24 | fil+ | fil+ | fil+ | fil− |
| *Candida parapsilosis* | 3 | b+ | b+ | b+ | b+ |
| | 24 | fil+ | fil+ | fil+ | fil− |
| *Cryptococcus neoformans** | 18 | brn | brn | brn | brn |
| *Cryptococcus laurentii* | 18 | crm | crm | crm | crm |
| *Cryptococcus albidus* | 18 | crm | crm | crm | crm |

TABLE 2-continued

MORPHOLOGY AND PIGMENT PRODUCTION ON MINIATURIZED
SOC MEDIUM AT VARIOUS CONCENTRATIONS OF CAFFEIC ACID

| | | Weight Percent Caffeic Acid | | | |
|---|---|---|---|---|---|
| Organism | Incubation Time (hrs.) | 0.006 | 0.06 | 0.12 | 0.6 |
| *Cryptococcus diffluens* | 18 | crm | crm | crm | crm |

*Twenty (20) strains were tested
gt = germ tube; fil = filament; cm = chlamydospore, ps = pseudohyphae b = blastospore, brn = brown, crm = cream

EXAMPLE 3

This example was performed to determine the effects of ammonium chloride addition to SOC medium on chlamydospore production by *Candida albicans*.

The test medium of the present example was prepared as follows: 20 grams of agar, 10 grams of oxgall, 10 grams of purified saponin, 0.6 grams caffeic acid, and varying concentrations of ammonium chloride, indicated in Table 3 below, were added to one liter of deionized water. The mixture was then stirred, heated to boiling, adjusted to a final pH of about 7.2, and sterilized by heating to 121° C. at 15 psi for 15 minutes. After a cooling period, about 5 milliliters of cooled medium was dispensed into the miniature plates as described in Example 1. These plates may be stored up to 8 months when stored as described in Example 1.

One to four yeast colonies grown on Sabouraud dextrose agar were plated as described in Example 1 on SOC medium containing the various concentrations of ammonium chloride listed in Table 3 below. At 1.0 M ammonium chloride, some of the medium components precipitated making it impossible to test that formulation. The yeast colonies so plated comprised 20 different strains of *Candida albicans* which had, on occasion, given negative or weak chlamydospore production. The plates were incubated for 3 hours at 37° C. and examined for germ tube formation. All 20 strains produced numerous germ tubes on all concentrations of ammonium chloride listed in Table 3. The plates were then incubated at room temperature for 24 to 72 hours and examined for chlamydospore production by the methods described in Example 1 and at the time intervals indicated in Table 3 below.

As can be seen by examination of Table 3, the addition of ammonium chloride significantly enhanced chlamydospore production. The optimum time for determining chlamydospore production was 24 hours to 48.

TABLE 3

EFFECTS ON NH$_4$Cl ADDITION TO SOC ON
CHLAMYDOSPORE PRODUCTION IN TWENTY STRAINS
OF *Candida albicans*
Chlamydospore Production
NH$_4$Cl. Molarity

| | | 0 | 0.001 | 0.01 | 0.1 |
|---|---|---|---|---|---|
| Incubation Time (hrs.) | No. of Strains | % Positive | % Positive | % Positive | % Positive |
| 24 | 20 | 45.0 | 80.0 | 100.0 | 50.0 |
| 48 | 20 | 60.0 | 100.0 | 100.0 | 80.0 |
| 72 | 20 | 100.0 | 100.0 | 100.0 | 100.0 |

EXAMPLE 4

This example was performed in order to test the ability of the miniaturized carbohydrate assimilation media of the present invention, performed by the method of the present invention, to differentiate between *Candida albicans* and *Candida stellatoidea*.

The miniaturized sucrose assimilation media employed in this example was prepared by adding 20 grams of agar, 20 milligrams of bromcresol purple, 0.67 grams yeast nitrogen base and 4 milliliters of 0.5 N sodium hydroxide to one liter of deionized water and adjusting to a pH of about 7.2. The media was sterilized by heating to about 121° C. at 15 psi for 15 minutes and after cooling, presterilized sucrose is added asceptically to yield a final sucrose concentration of 1.0 percent. The media was then dispensed in about 5 milliliter aliquots into the miniature plates, as described above. These plates may be stored, by the method described in Example 1, up to eight months without dehydration or loss of color.

Six species of Candida were first grown on Sabouraud dextrose agar containing gentamicin, as previously described. Yeasts were taken from this primary growth medium and suspended in sterile deionized water and held for at least one hour at room temperature for purposes of prestarvation. After prestarvation, the suspension was vortexed and, using a sterile pipet, one to about three drops of yeast suspension was placed onto the surface of the miniaturized sucrose media. The plates were then incubated at room temperature for 4 to 6 hours. Following the incubation period the plates were checked for color change from purple to yellow indicating sucrose assimilation. The plates were held at room temperature for 24 hours and read a second time.

The results of this example are shown in Table 4A below. *Candida albicans, Candida stellatoidea, Candida tropicalis, Candida krusei* and *Candida glabrata* gave the correct assimilation response on the miniaturized sucrose assimilation plates after 5 hours incubation at room temperature and maintained the correct response for 24 hours. *Candida parapsilosis*, however, did not show a characteristic positive reaction until 18 to 24 hours. From this data, it is apparent that *Candida albicans* and *Candida stellatoidea* can be differentiated in 5 hours.

TABLE 4A

EXAMINATION OF THE MINIATURE SUCROSE ASSIMILATION PLATE WITH VARIOUS YEASTS

| Organism | No. of Isolates | Correct Response | Sucrose Assimilation | | | | | | | |
|---|---|---|---|---|---|---|---|---|---|---|
| | | | 5 hr. | | | | 24 hr. | | | |
| | | | + | | − | | + | | − | |
| | | | No. | % | No. | % | No. | % | No. | % |
| C. albicans | 120 | + | 120 | 100.0 | 0 | 0.0 | 120 | 100.0 | 0 | 0.0 |
| C. stellatoidea | 21 | − | 0 | 0.0 | 21 | 100.0 | 0 | 0.0 | 21 | 100.0 |
| C. tropicalis | 29 | + | 29 | 100.0 | 0 | 0.0 | 29 | 100.0 | 0 | 0.0 |
| C. parapsilosis | 31 | + | 0 | 0.0 | 31 | 100.0 | 31 | 100.0 | 0 | 0.0 |
| C. krusei | 18 | − | 0 | 0.0 | 18 | 100.0 | 0 | 0.0 | 18 | 100.0 |
| C. glabrata | 34 | − | 0 | 0.0 | 34 | 100.0 | 0 | 0.0 | 34 | 100.0 |

To further pursue the concept of miniature assimilation for other carbohydrates besides sucrose, identical experiments were performed where media were prepared as described above except that 1 gram of each sugar listed below in Table 4B was substituted for sucrose to yield a specific sugar containing medium. Yeasts were inoculated, plated and grown as described above and examined for carbohydrate assimilation at the time indicated in Table 4B below.

As shown in Table 4B, the proper assimilation pattern for each species can be achieved within 24 hours. With Candida parapsilosis, there was a discrepancy with the positive sucrose assimilation at 5 hours and the negative results in the previous experiment as given in Table 4A. This is a significant example of strain variation among yeast strains.

The plates were inoculated with four species of Cryptococcus and six species of Candida, by transferring, with a sterile cotton swab, two to three yeast colonies from a general growth medium such as Sabouraud dextrose agar. Two to three yeasts of a single species were inoculated per plate and the plates were incubated at 35° C. for up to 24 hours.

The results of this example are shown in Table 5. The Cryptococcus species were positive in one hour and the other yeast isolates remained negative for 24 hours. A hydrolysis of urea releases ammonium gas which is basic and rapidly spreads throughout the medium turning the medium from orange to pink. A positive organism completely changes the medium color in the miniature plate within two to three hours. Therefore, if more than one organism is inoculated onto the miniaturized urease plate, the plate must be read between about one and two hours or false positive reactions can occur.

TABLE 4B

EXAMINATION OF MINIATURE CARBOHYDRATE ASSIMILATION PLATES WITH VARIOUS YEASTS

| Organism | No. of Isolates | Carbohydrate* | Correct Response | Assimilation | | | | | | | |
|---|---|---|---|---|---|---|---|---|---|---|---|
| | | | | 5 hr. | | | | 24 hr. | | | |
| | | | | + | | − | | + | | − | |
| | | | | No. | % | No. | % | No. | % | No. | % |
| C. albicans | 3 | suc | + | 3 | 100.0 | 0 | 0.0 | 3 | 100.0 | 0 | 0.0 |
| | | malt | + | 3 | 100.0 | 0 | 0.0 | 3 | 100.0 | 0 | 0.0 |
| | | galac | + | 3 | 100.0 | 0 | 0.0 | 3 | 100.0 | 0 | 0.0 |
| | | treh | + | 2 | 66.7 | 1 | 33.3 | 3 | 100.0 | 0 | 0.0 |
| | | lac | − | 0 | 0.0 | 3 | 100.0 | 0 | 0.0 | 3 | 100.0 |
| C. stellatoidea | 3 | suc | − | 0 | 0.0 | 3 | 100.0 | 0 | 0.0 | 3 | 100.0 |
| | | malt | + | 3 | 100.0 | 0 | 0.0 | 3 | 100.0 | 0 | 0.0 |
| | | galac | + | 3 | 100.0 | 0 | 0.0 | 3 | 100.0 | 0 | 0.0 |
| | | treh | + | 0 | 0.0 | 3 | 100.0 | 3 | 100.0 | 0 | 0.0 |
| | | lac | − | 0 | 0.0 | 3 | 100.0 | 0 | 0.0 | 3 | 100.0 |
| C. tropicalis | 3 | suc | + | 3 | 100.0 | 0 | 0.0 | 3 | 100.0 | 0 | 0.0 |
| | | malt | + | 3 | 100.0 | 0 | 0.0 | 3 | 100.0 | 0 | 0.0 |
| | | galac | + | 1 | 33.3 | 2 | 66.7 | 3 | 100.0 | 0 | 0.0 |
| | | treh | + | 1 | 33.3 | 2 | 66.7 | 3 | 100.0 | 0 | 0.0 |
| | | lac | − | 0 | 0.0 | 3 | 100.0 | 0 | 0.0 | 3 | 100.0 |
| C. parapsilosis | 3 | suc | + | 3 | 100.0 | 0 | 0.0 | 3 | 100.0 | 0 | 0.0 |
| | | malt | + | 1 | 33.3 | 2 | 66.7 | 3 | 100.0 | 0 | 0.0 |
| | | galac | + | 2 | 66.7 | 1 | 33.3 | 3 | 100.0 | 0 | 0.0 |
| | | treh | + | 0 | 0.0 | 3 | 100.0 | 3 | 100.0 | 0 | 0.0 |
| | | lac | − | 0 | 0.0 | 3 | 100.0 | 0 | 0.0 | 3 | 100.0 |

*suc = sucrose; malt = maltose; galac = galactose; treh = trehalose; lac = lactose

EXAMPLE 5

This example was performed to test the ability of miniaturized urease media to detect the presence of the urease enzyme in various species of Cryptococcus.

The miniature urease plates in the present example were made by preparing urea agar according to manufacturer's instructions, sterilizing by heating at 121° C. at 15 psi for 15 minutes and then dispensing the media into the plates as described in the previous examples. Again, by storing as described in Example 1, the plates remain stable for up to at least 8 months.

TABLE 5

EXAMINATION OF THE MINIATURE UREASE PLATE WITH VARIOUS YEASTS

| Organism | No. of Isolates | Correct Response | Urease Hydrolysis* | | | |
|---|---|---|---|---|---|---|
| | | | + | | − | |
| | | | No. | % | No. | % |
| Cr. neoformans | 81 | + | 81 | 100.00 | 0 | 0.0 |
| Cr. albidus | 20 | + | 20 | 100.0 | 0 | 0.0 |
| Cr. laurentii | 10 | + | 10 | 100.00 | 0 | 0.0 |
| Cr. diffluens | 24 | + | 24 | 100.00 | 0 | 0.0 |

TABLE 5-continued
EXAMINATION OF THE MINIATURE UREASE PLATE WITH VARIOUS YEASTS

| Organism | No. of Isolates | Correct Response | Urease Hydrolysis* + No. | + % | − No. | − % |
|---|---|---|---|---|---|---|
| C. albicans | 122 | — | 0 | 0.0 | 122 | 100.0 |
| C. stellatoidea | 21 | — | 0 | 0.0 | 21 | 100.0 |
| C. tropicalis | 29 | — | 0 | 0.0 | 29 | 100.0 |
| C. parapsilosis | 32 | — | 0 | 0.0 | 32 | 100.0 |
| C. krusei | 18 | −(+)** | 0 | 0.0 | 18 | 100.0 |
| C. glabrata | 34 | — | 0 | 0.0 | 34 | 100.0 |

*The reactions were read at one hour and negative reactions were reconfirmed at 24 hours.
**C. krusei has been reported to rarely show a positive urease reaction, but the strains used in this experiment were negative.

EXAMPLE 6

This example was performed to compare the post-incubation addition of dye for detection of carbohydrate assimilation with conventional carbohydrate assimilation methods. The carbohydrate assimilations detected by post-incubation addition of dye were conducted in Microtiter ™ plates and are, hence, referred to as "Microtiter ™ carbohydrate agar assimilation" in the text and Tables 6A and 6B, below.

The Microtiter ™ carbohydrate assimilation media employed in this example were prepared by adding 20 grams of agar and 0.67 grams of yeast nitrogen base to 950 milliliters deionized water. The mixture was stirred with heat to dissolve the ingredients, adjusted to a pH of about 7.2 with 0.5 N NaOH, divided into eight equal parts, sterilized at 121° C. at 15 psi for 15 minutes and, thereafter, allowed to cool to about 45° to 55° C. Then, 6.25 milliliters of a two percent, filter sterilized, carbohydrate solution containing one of each of the eight carbohydrates listed in Table 6A or 6B, below, was asceptically added to one of each of the cooled solutions. The two percent carbohydrate solutions were prepared by adding 0.2 grams of carbohydrate to 10 milliliters deionized water and adjusting to a pH of about 7.0 with 0.05 N NaOH. After mixing, 0.15 milliliters aliquots of the carbohydrate-containing medium was sterily dispensed into the wells of a Microtiter ™ plate.

The yeast listed in Tables 6A and 6B, below, were taken from plates containing a general yeast growth medium as described in Example 4 and suspended at a concentration of McFarland No. 8, approximately $10^8$ organisms, in $1 \times 10^{-5}$ M NaOH and held for about one hour at room temperature for purposes of prestarvation. Following prestarvation, the suspension was vortexed and 0.02 milliliter aliquots were aseptically transferred into each medium containing well of the Microtiter ™ plate. The plates were covered with a sterile lid and incubated at room temperature for 24 hours. After incubation, 0.02 milliliter aliquots of filter sterilized, 20 micrograms bromcresol purple per milliliter dye solution was added to each well of the Microtiter ™ plates. The plates were read 5 to 10 minutes after dye addition for a purple to yellow color change indicative of positive assimilation of carbohydrate.

The results of the Microtiter ™ carbohydrate agar assimilations are given in Tables 6A and 6B, below, wherein the data are compared to reports for conventional methods given in *The Yeasts* by Lodder and the A.P.I. 20C Strip. The conventional methods include, Wickerham liquid, Saito agar, and auxanographic technique.

TABLE 6A
COMPARISON OF MICROTITER ™ CARBOHYDRATE AGAR ASSIMILATION WITH REPORTS FROM CONVENTIONAL ASSIMILATION METHODS*

| Organism | No. of Isolates | System | dextrose | galactose | sucrose | maltose | cellibiose | trehalose | lactose | raffinose |
|---|---|---|---|---|---|---|---|---|---|---|
| C. albicans | — | Conventional | + | + | + | + | − | + | − | − |
|  | 45 | Microtiter | + | + | + | + | − | + | − | − |
| C. stellatoidea | — | Conventional | + | + | − | + | − | + | − | − |
|  | 12 | Microtiter | + | + | − | + | − | + | − | − |
| C. tropicalis | — | Conventional | + | + | + | + | v | + | − | − |
|  | 32 | Microtiter | + | + | + | + | ∓ | + | − | − |
| C. parapsilosis | — | Conventional | + | + | + | + | − | + | − | − |
|  | 12 | Microtiter | + | + | + | + | − | + | − | − |
| C. krusei | — | Conventional | + | − | − | − | − | − | − | − |
|  | 8 | Microtiter | + | − | − | − | − | − | − | − |
| C. glabrata | — | Conventional | + | − | − | − | − | + | − | − |
|  | 16 | Microtiter | + | − | − | − | − | + | − | − |
| Cr. neoformans | — | Conventional | + | + | + | + | w | + | − | w |
|  | 8 | Microtiter | + | + | + | + | ∓ | ± | − | − |
| Cr. laurentii | — | Conventional | + | + | + | + | + | + | + | + |
|  | 2 | Microtiter | + | + | + | + | + | + | + | + |
| Cr. albidus var. diffluens | — | Conventional | + | w | + | + | + | + | w | w |
|  | 7 | Microtiter | + | ∓ | + | + | ± | + | − | − |

*Conventional Methods: Wickerham liquid method, Saito agar method, auxanographic method.
**v = variable; w = weak; ± = ≧50%; ∓ = ≦50%

6.25 milliliters of a two percent, filter sterilized, carbo-

TABLE 6B
COMPARISON OF MICROTITER ™ CARBOHYDRATE AGAR ASSIMILATION WITH A.P.I. 20C STRIP REPORTS

| Organism | Total No. of Isolates | System | dextrose No. | dextrose % | galactose No. | galactose % | sucrose No. | sucrose % | maltose No. | maltose % | cellibiose No. | cellibiose % | trehalose No. | trehalose % | lactose No. | lactose % | raffinose No. | raffinose % |
|---|---|---|---|---|---|---|---|---|---|---|---|---|---|---|---|---|---|---|
| C. albicans | —* | API | — | 100 | — | 100 | — | 96 | — | 100 | — | 0 | — | 99 | — | 0 | — | 0 |
|  | 45 | Microtiter | 45 | 100 | 45 | 100 | 45 | 100 | 45 | 100 | 0 | 0 | 45 | 100 | 0 | 0 | 0 | 0 |

TABLE 6B-continued
COMPARISON OF MICROTITER ™ CARBOHYDRATE AGAR ASSIMILATION WITH A.P.I. 20C STRIP REPORTS

| Organism | Total No. of Isolates | System | Assimilation at 24 hrs. | | | | | | | | | | | | | | |
|---|---|---|---|---|---|---|---|---|---|---|---|---|---|---|---|---|---|
| | | | dextrose | | galactose | | sucrose | | maltose | | cellibiose | | trehalose | | lactose | | raffinose | |
| | | | No. | % | No. | % | No. | % | No. | % | No. | % | No. | % | No. | % | No. | % |
| C. stellatoidea | — | API | — | 100 | — | 100 | — | 0 | — | 100 | — | 0 | — | 1 | — | 0 | — | 0 |
| | 12 | Microtiter | 12 | 100 | 12 | 100 | 0 | 0 | 12 | 100 | 0 | 0 | 12 | 100 | 0 | 0 | 0 | 0 |
| C. tropicalis | — | API | — | 100 | — | 99 | — | 100 | — | 100 | — | 12 | — | 100 | — | 0 | — | 0 |
| | 32 | Microtiter | 32 | 100 | 32 | 100 | 32 | 100 | 31 | 97 | 15 | 47 | 32 | 100 | 0 | 0 | 0 | 0 |
| C. parapsilosis | — | API | — | 100 | — | 100 | — | 100 | — | 100 | — | 0 | — | 97 | — | 0 | — | 0 |
| | 12 | Microtiter | 12 | 100 | 12 | 100 | 12 | 100 | 12 | 100 | 0 | 0 | 12 | 100 | 0 | 0 | 0 | 0 |
| C. krusei | — | API | — | 100 | — | 0 | — | 0 | — | 0 | — | 0 | — | 0 | — | 0 | — | 0 |
| | 8 | Microtiter | 8 | 100 | 0 | 0 | 0 | 0 | 0 | 0 | 0 | 0 | 0 | 0 | 0 | 0 | 0 | 0 |
| C. glabrata | — | API | — | 100 | — | 0 | — | 0 | — | 0 | — | 0 | — | 99 | — | 0 | — | 0 |
| | 16 | Microtiter | 16 | 100 | 0 | 0 | 0 | 0 | 0 | 0 | 0 | 0 | 16 | 100 | 0 | 0 | 0 | 0 |
| Cr. neoformans | — | API | — | 100 | — | 99 | — | 100 | — | 100 | — | 37 | — | 73 | — | 0 | — | 86 |
| | 8 | Microtiter | 8 | 100 | 8 | 100 | 8 | 100 | 8 | 100 | 1 | 13 | 4 | 50 | 0 | 0 | 0 | 0 |
| Cr. laurentii | — | API | — | 100 | — | 100 | — | 100 | — | 92 | — | 92 | — | 92 | — | 99 | — | 99 |
| | 2 | Microtiter | 2 | 100 | 2 | 100 | 2 | 100 | 2 | 100 | 2 | 100 | 2 | 100 | 2 | 100 | 2 | 100 |
| Cr. albidus var. diffluens | — | API | — | 100 | — | 0 | — | 100 | — | 99 | — | 99 | — | 93 | — | 0 | — | 68 |
| | 7 | Microtiter | 7 | 100 | 2 | 29 | 7 | 100 | 7 | 100 | 6 | 86 | 7 | 100 | 0 | 0 | 0 | 0 |

*Total number of isolates given only in A.P.I. databank.

As shown in Table 6A above, there is good correlation between the Microtiter ™ carbohydrate agar assimilation test and the published results of conventional Wickerham liquid, Saito agar and auxanographic methods. Certain carbohydrate reactions with *Cr. neoformans* and *Cr. albidus*, however, require examination.

As shown in Table 6B, above, there is an overall good correlation between the Microtiter ™ carbohydrate agar assimilation test and the A.P.I. 20C strip method with the exceptions of raffinose assimilation for *Cr. neoformans* and *Cr. albidus*.

EXAMPLE 7

This example was performed in order to test the effect of an increased ratio of surface area of organisms to volume of medium on the time-to-positivity in carbohydrate assimilation. One way to demonstrate the effect of said increased ratio is to hold the surface area and microbial inoculum constant while varying the volume, herein expressed as depth of medium, in a given test plate or tube.

Three different containers were used to examine the effect of surface area to volume ratios on time-to-positivity: the miniaturized culture plates of the present invention, standard 100×15 millimeters petri plates, and standard 16×125 millimeter flat-bottom culture tubes. The theoretical limits of the surface area to volume ratio employed in a given container will be set by the dimensions necessary to visualize the color change prompted by positive carbohydrate assimilation and a minimal depth necessary to preclude dehydration of the medium.

Sucrose assimilation medium prepared as described in Example 4, above, was aseptically poured into each of the containers at the depths shown in FIG. 13.

*Candida albicans*, the test organism, was first grown on Sabouraud dextrose agar containing gentamicin, as previously described. Yeasts were taken from this primary growth medium and suspended in sterile deionized water and held at least one hour at room temperature for purposes of prestarvation. Following prestarvation, the suspension was vortexed and, using a sterile pipet, one to about three drops of yeast suspension was placed onto the surface of each miniaturized plate and culture tube containing sucrose medium and three one-drop inoculations of yeast were placed on each 100×15 millimeter (mm) petri plate containing sucrose medium. The plates and tubes were then incubated at room temperature for not more than 12 hours. Each plate or tube of the depth specified in the graph in FIG. 13, was run in duplicate. Positive reactions, denoting sucrose assimilation, were determined by an obvious color change from purple to yellow at the post-inoculation time intervals shown in the graph in FIG. 13, given as "Time-to-Positivity" in hours.

The results of this example are shown in the graph in FIG. 13. This example confirms that at a medium depth range of 2 to 2.5 mm, approximately 4 to 5 milliliters of medium per plate, in the miniaturized plates (0—0), the time-to-positivity for sucrose assimilation by *Candida albicans* is from about four to five hours. Although a shift in the time-to-positivity is seen with increasing depth or volume at a constant surface area of organisms in the miniaturized plates, the most dramatic effect of increased medium depth or volume at a constant surface area of organisms is seen in the standard 100×15 mm petri plates (Δ—Δ). Additionally, the medium depth in the standard petri plate is typically 5 mm corresponding to 18 to 20 milliliters of medium per 100×15 mm plate which is shown to yield about a 10 hour time-to-positivity for *Candida albicans* in the sucrose assimilation test. Furthermore, medium depths of 3 mm or less in the 100×15 mm petri plates are not preferred due to possible problems with dehydration during storage. The greater time-to-positivity seen in the 16×125 mm flat-bottom culture tubes (■—■) is thought to be due to problems with oxygen tension created by the closed environment of the culture tubes as compared to the open system of the plates.

We claim:

1. A culture container of a size to fit on a conventional microscope viewing stand for the identification of fungal pathogens, comprising:
   (a) a well means for containing fungal differentiation media, the dimensions of said well means adapted to contain a quantity of up to about 5.0 milliliters of media at a depth of up to about 4.5 millimeters, for the growth of a specimen; and
   (b) a fungal differentiation media present in said well means in the amount of said quantity comprising a composition effective to induce a different observable effect in at least one species of fungi as compared with another species of fungi and effective to induce germ tube production and conventional morphological characteristics, said composition including purified saponin, oxgall, a substrate for phenol oxidase in sufficient quantity to allow differentiation of *Cryptococus neoformans*, water and ammonium ions.

2. The culture container of claim 1, further comprising a lid adapted to removable engage with said container.

3. The culture container of claim 1, wherein said fungal differentiation media further comprises a carrying agent.

4. The culture container of claim 1, wherein said substrate for phenol oxidase is caffeic acid.

5. The culture container of claim 1, wherein said substrate for phenol oxidase comprises from about 0.005 to about 0.5 weight percent of the weight of said water.

6. The culture container of claim 5, wherein said substrate for phenol oxidase comprises from about 0.012 to about 0.12 weight percent of the weight of said water.

7. The culture container of claim 6, wherein said substrate for phenol oxidase comprises about 0.06 weight percent of the weight of said water.

8. The culture container of claim 1, wherein said saponin comprises from about 0.1 to about 5.0 weight percent of the weight of said water.

9. The culture container of claim 8, wherein said saponin comprises from about 0.1 to about 2.5 weight percent of the weight of said water.

10. The culture container of claim 9, wherein said saponin comprises about 1.0 weight percent of the weight of said water.

11. The culture container of claim 3, wherein said carrying agent is present in an amount of from about 1.0 to about 5.0 weight percent of the weight of said water.

12. The culture container of claim 11, wherein said carrying agent is present in an amount of 2.0 weight percent of the weight of said water.

13. The culture container of claim 3, wherein said carrying agent is agar.

14. The culture container of claim 1, wherein said oxgall is present in an amount from about 0.25 to about 30.0 weight percent of the weight of said water.

15. The culture container of claim 14, wherein said oxgall is present in an amount from about 0.5 to about 5.0 weight percent of the weight of said water.

16. The culture container of claim 15, wherein said oxgall is present in an amount of about 1.0 weight percent of the weigth of said water.

17. The culture container of claim 1, wherein said ammonium ions are present in an amount from 0.001 M to about 0.5 M.

18. The culture container of claim 17, wherein said ammonium ions are present from about 0.005 M to about 0.05 M.

19. The culture container of claim 18, wherein said ammonium ions are present at about 0.01 M.

20. The culture container of claim 1, wherein said well means is cylindrical.

21. The culture container of claim 1, wherein said well means is pie-shaped.

22. The culture container of claim 1, wherein said well means has a perimeter of rectangular or square shape.

23. The culture container of claim 1, further comprising at least one additional well means for containing fungal differentiation media.

24. The culture container of claim 1, wherein said quantity is from about 2.5 milliliters to about 5.0 milliliters at a depth of up to about 4.5 millimeters.

25. The culture container of claim 23 further comprising at least one additional media for fungal differentiation or growth, each of said additional medias situated in one of said additional well means.

26. The culture container of claim 23, wherein a second fungal differentiation media is present in at least one of said additional well means in the amount of said quantity comprising a media effective to induce a different observable effect in at least one species of fungi subjected to a previous carbohydrate depletion step as compared to another species of fungi subjected to said carbohydrate depletion step, wherein said second fungal differentiation media is adapted in composition to produce an observable effect of positive or negative carbohydrate assimilation in carbohydrate depleted fungal cells within from about 3 hours to about 24 hours from inoculation.

27. The culture container of claim 23 wherein a second fungal differentiation media is present in at least one of said additional well means in the amount of said quantity comprising a media adapted in composition to induce a different observable effect in a fungal species metabolizing urea as compared to a fungal species which does not within from about 1 hour to about 3 hours after inoculation.

28. The culture container of claim 23 wherein a second fungal differentiation media is present in at least one of said additional well means in the amount of said quantity comprising a media effective to induce a different observable effect in at least one species of fungi subjected to a previous carbohydrate depletion step as compared to another species of fungi subjected to said carbohydrate depletion step, wherein said second fungal differentiation media is adapted in composition to produce an observable effect to positive or negative carbohydrate assimilation in carbohydrate depleted fungal cells within from about 3 to about 24 hours from inoculation, and a third fungal differentiation media is present in another of said additional well means adapted in composition to induce a different observable effect in a fungal species metabolizing urea as compared to a fungal species which does not within from about 1 hour to about 3 hours after inoculation.

29. A culture container of a size to fit on a conventional microscope viewing stand for the identification of fungal pathogens, comprising:

(a) a well means for containing fungal differentiation media, the dimensions of said well means adapted to contain a quantity of up to about 5.0 milliliters of media at a depth of up to about 4.5 millimeters, for the growth of a specimen; and (b) a fungal differentiation media present in said well means in the amount of said quantity, comprising about 1.0 weight percent purified saponin, about 1.0 weight percent oxgall, about 0.06 weight percent caffeic acid, about 0.01 M ammonium ions, about 2.0 weight percent agar, and water, said weight percentages based on the weight of said water.

30. A culture container of a size to fit on a conventional microscope viewing stand for the identification of fungal pathogens, comprising:

(a) at least two well means for containing fungal differentiation media, the dimensions of each of said two well means adapted to contain a quantity of up to about 5.0 milliliters of media at a depth of up to about 4.5 millimeters, each of said well means for the growth of a specimen; and (b) a first fungal differentiation media present in one of said well means in the amount of said quantity comprising purified saponin, oxgall, a substrate for phenol oxidase, ammonium ions, a carrying agent, and water, and a second fungal differentiation media present in the other of said well means in the amount of said quantity comprising a media effective to induce a different observable effect in at least one species of fungi subjected to a previous carbohydrate depletion step as compared to another species of fungi subjected to said carbohydrate depletion step, wherein said second fungal differentiation media is adapted in composition to produce an observable effect of positive or negative carbohydrate assimilation in carbohydrate depleted fungal cells within from about 3 hours to about 24 hours from inoculation.

31. The culture container of claim 30, further comprising a lid adapted to removably engage with said container.

32. The culture container of claim 30, wherein said quantity is from about 2.5 milliliters to about 5.0 milliliters at a depth of up to about 4.5 millimeters.

33. A culture container of a size to fit on a conventional microscope viewing stand for the identification of fungal pathogens, comprising:

(a) at least two well means for containing fungal differentiation media, the dimensions of each of said two well means adapted to contain a quantity of up to about 5.0 milliliters of media at a depth of up to about 4.5 millimeters, each of said well means for the growth of a specimen; and (b) a first fungal differentiation media present in one of said well means in the amount of said quantity comprising purified saponin, oxgall, a substrate for phenol oxidase, ammonium ions, a carrying agent, and water, and a second fungal differentiation media present in the other of said well means in the amount of said quantity comprising a media adapted in composition to induce a different observable effect in a fungal species metabolizing urea as compared to a fungal species which does not within from about 1 hour to about 3 hours after inoculation.

34. The culture container of claim 33, further comprising a lid adapted to removably engage with said container.

35. The culture container of claim 33, wherein said quantity is from about 2.5 milliliters to about 5.0 milliliters at a depth of up to about 4.5 millimeters.

36. A culture container of a size to fit on a conventional microscope viewing stand for the identification of fungal pathogens comprising:

(a) at least three well means for containing fungal differentiation media, the dimensions of each of said three well means adapted to contain a quantity of up to about 5.0 milliliters of media at a depth of up to about 4.5 millimeters, each of said well means for the growth of a specimen; and (b) a first fungal differentiation media present in one of said well means in the amount of said quantity comprising purified saponin, oxgall, a substrate for phenol oxidase, ammonium ions, a carrying agent, and water, a second fungal differentiation media present in another of said well means in the amount of said quantity comprising a media effective to induce a different observable effect in at least one species of fungi subjected to a previous carbohydrate depletion step as compared to another species of fungi subjected to said carbohydrate depletion step, wherein said second fungal differentiation media is adapted in compositin to produce an observable effect of positive or negative carbohydrate assimilation in carbohydrate depleted fungal cells within from about 3 to about 24 hours from inoculation, and a third fungal differentiation media in the third of said well means adapted in composition to induce a different observable effect in a fungal species metabolizing urea as compared to a fungal species which does ot within from about 1 hour to about 3 hours after inoculation.

37. The culture container of claim 36, further comprising a lid adapted to removably engage with said container.

38. The culture container of claim 36, wherein said quantity is from about 2.5 milliliters to about 5.10 milliliters at a depth of up to about 4.5 millimeters.

* * * * *

UNITED STATES PATENT AND TRADEMARK OFFICE
CERTIFICATE OF CORRECTION

PATENT NO. : 4,728,607            Page 1 of 2

DATED : March 1, 1988

INVENTOR(S) : Gordon L. Dorn, et al.

It is certified that error appears in the above-identified patent and that said Letters Patent is hereby corrected as shown below: Title page:

In the Abstract, 4th line, change "induce germ tube production in" to --allow differentiation of"; insert --neoformans-- after "Cryptococcus"; italicize Cryptococcus neoformans.

Col. 3, line 66, "Cryptococcus" should be italicized.

Col. 4, line 8, "Cryptococcus" should be italicized.

Col. 4, line 10, "Cryptococcus" should be italicized.

Col. 4, line 23, "Cryptococcus" should be italicized.

Col. 4, line 27, "or" should be --for--.

Col. 4, line 27, "Cryptococcus" should be italicized.

Col. 4, line 45, "incicated" should be --indicated--.

Col. 4, line 46, "Tne" should be --The--.

Col. 4, line 66, "Tnis" should be --This--.

Col. 5, line 29, "Cryptococcus" and "Candida" should be italicized.

Col. 6, line 52, "ous!y" should be --ously--.

Col. 6, line 58, "or" should be --of--.

Col. 8, line 52, after "14b" insert --or--.

Col. 8, line 54, "respestively" should be --respectively--.

Col. 10, line 1, "han" should be --than--.

Col. 10, line 13, "pnenol" should be --phenol--.

Col. 11, line 12, "phenor" should be --phenol--.

Col. 13, line 45, "108" should be --$10^8$--.

Col. 14, line 37, "incubatior" should be --incubation--.

UNITED STATES PATENT AND TRADEMARK OFFICE
CERTIFICATE OF CORRECTION

PATENT NO.  :   4,728,607

DATED       :   March 1, 1988

INVENTOR(S) :   Gordon L. Dorn, et al.

It is certified that error appears in the above-identified patent and that said Letters Patent is hereby corrected as shown below:

Col. 30, line 54, "5.10" should be --5.0--.

Col. 14, line 42, "colorless" should be --yellow--.

Col. 14, line 43, "yellow" should be --colorless--.

Col. 14, line 57, "mg" should be --micrograms--.

Col. 15, line 49, after "will" delete "not".

Col. 18, line 21, "Candida" and "Cryptococcus" should be italicized.

Table 2, first line (*Candida* *albicans* 3 hour incubation time, under 0.12) "gt-+" should be --gt+--.

Col. 20, line 44, "Candida" should be italicized.

Col. 21, line 61, "Cryptococcus" should be italicized.

Col. 22, lines 15-16, "Cryptococcus" and "Candida" should be italicized.

Col. 27, line 21, "Cryptococus" should be --Cryptococcus--.

Col. 27, line 25, "removable" should be --removably--.

Col. 28, line 57, "effect to" should be --effect of--.

Col. 30, line 40, "compositin" should be --composition--.

Col. 30, line 48, "ot" should be --not--.

Signed and Sealed this

Thirteenth Day of December, 1988

*Attest:*

DONALD J. QUIGG

*Attesting Officer*         *Commissioner of Patents and Trademarks*